United States Patent [19]

Townsend et al.

[11] 3,948,897

[45] Apr. 6, 1976

[54] SYNTHESIS OF 1-(TETRAHYDRO-2-FURANYL)-5-FLUOROURACIL (FTORAFUR) VIA DIRECT FLUORINATION

[75] Inventors: Leroy B. Townsend; Robert A. Earl, both of Salt Lake City, Utah

[73] Assignee: The United States of America as represented by the Secretary of Health, Education and Welfare, Washington, D.C.

[22] Filed: Oct. 9, 1973

[21] Appl. No.: 405,532

[52] U.S. Cl. .............................................. 260/260
[51] Int. Cl.² ...................................... C07D 239/52
[58] Field of Search .................................... 260/260

[56] References Cited
UNITED STATES PATENTS
3,682,917  8/1972  Kruniants........................... 260/260
FOREIGN PATENTS OR APPLICATIONS
1,168,391  10/1969  United Kingdom Primary Examiner—Richard J. Gallagher
Assistant Examiner—Anne Marie T. Tighe
Attorney, Agent, or Firm—John S. Roberts, Jr.; Norman J. Latker; Thomas G. Ferris

[57] ABSTRACT

A facile process for the production of Ftorafur [1-(tetrahydro-2-furanyl)-5-fluorouracil] which comprises reacting 2,4-bis-trimethylsilyl uracil with 2-chlorotetrahydrofuran to produce 1-tetrahydro-2-furanyluracil at low temperatures in a dry non-aqueous solvent, e.g. a halogenated hydrocarbon solvent such as methylene chloride. Subsequently the desired final product is produced by direct fluorination of the uracil ring as the last step utilizing a fluorinating agent such as trifluoromethylhypofluorite. This step is conducted in the cold and again in the presence of a halogenated hydrocarbon solvent such as chloroform. Ftorafur has been utilized as a pyrimidine analog for the management of carcinoma in the breast and large intestine and with less side effects than 5-fluorouracil (5-FU).

4 Claims, No Drawings

SYNTHESIS OF 1-(TETRAHYDRO-2-FURANYL)-5-FLUOROURACIL (FTORAFUR) VIA DIRECT FLUORINATION

In the management of malignant tumors, especially those in the breast and intestine, increasing emphasis has been placed upon developing and using compounds which were less toxic in some instances than the basic pyrimidine analog, 5-fluorouracil (5-FU) used presently for this purpose (cf. Aviado's Krantz and Carr, Pharmacological Principles of Medical Practice, 8th Edition, 1972, page 971).

The present invention is directed towards a process for producing such a compound related to 5-fluorouracil; namely, Ftorafur (Fluorofur) according to the reaction scheme A set out below. Ftorafur is a heterocyclic compound which is a furanidyl pyrimidine and has proved less toxic than 5-FU. Its antitumor activities are used principally in the treatment of breast cancer and tumors of the digestive tract and its antitumor properties are similar to those of the basic 5-FU compound. In its modus of action, apparently Ftorafur may block DNA synthesis at the thymidylate level.

slight molar surplus of the furan reactant is utilized, as, for example (1.08 mmoles : 1.00 mmoles : 1 ml). The product 1-(tetrahydro-2-furanyl)-5-fluorouracil (IV) is produced from III above by direct fluorination of the uracil ring utilizing as a fluorinating agent trifluoromethylhypofluorite, again under conditions using a halogenated hydrocarbon solvent and in the cold at $-78°$ C. (dry ice and acetone). The fluorite adduct is broken up after the reaction is completed by means of a mixture of ammonium hydroxide and methanol such as a 1 : 10 ratio of concentrated ammonium hydroxide to methanol. The product IV is extracted and recovered utilizing a halogenated hydrocarbon solvent such as chloroform.

SOLVENTS

In the reaction of 2-chlorotetrahydrofuran with 2,4-bistrimethylsilyl uracil, it has been found that the utilization of a dry non-aqueous solvent, e.g. a halogenated hydrocarbon, such as the preferred methylene chloride, has brought about increased results up to about 50% over published values as in the production of III (1-tetrahydro-2-furanyl uracil). Also, in the final step

REACTION SCHEME A

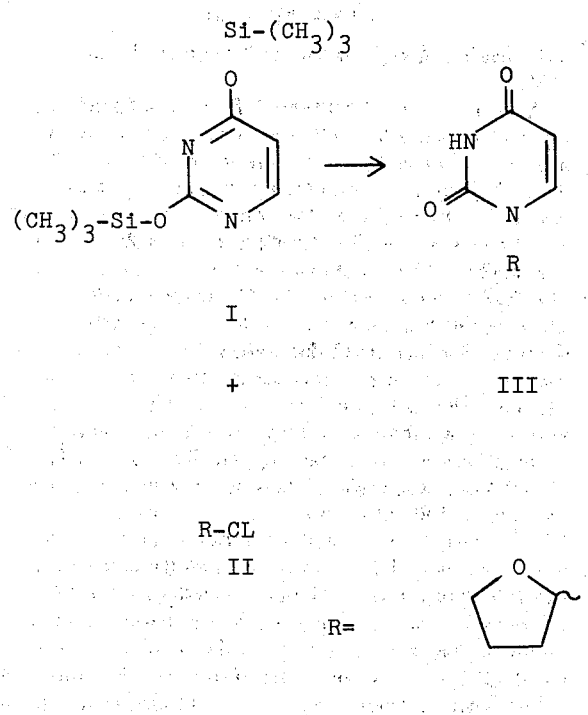

THE PROCESS

In the reaction scheme A above, reactant 2-chlorotetrahydrofuran (II) is condensed with 2,4-bistrimethylsilyl uracil (I) to yield 1-tetrahydro-2-furanyluracil (III). The reaction is conducted in the cold at about $-78°$ C. in the presence of a dry halogenated hydrocarbon such as methylene chloride. A wherein the Ftorafur is recovered from impurities, increased procedural results have been achieved by utilizing an organic solvent containing halogen such as chloroform to isolate the product. In both of these steps other halogen containing solvents may be utilized such as lower alkylene halides including methylene bromide, ethylene chloride, ethylene bromide, carbon tetrachloride, and chloroform.

PRIOR ART

Representative literature prior art with respect to Ftorafur, its structure, and medicinal utility is as follows:

1. Blokhina et al., "Results of Treatment of Malignant Tumors with Ftorafur," Cancer, 30, 390 (1972).
2. Smolyanskaya et al., "To Biological Activity of Antitumour Antimetabolite 'Ftoraful'," Neoplasma, 19, 341 (1972).
3. Sniker et al., "Analogs of Pyrimidine Nucleosides," Chem. Heterocycl. Com., (Russia), Eng. Ed., 5, 130 (1969).
4. Hiller et al., Dokl. Akad. Nauk. (USSR), 176, 332 (1967).

The patent prior art with respect to the process of making Ftorafur is also set out below:

3,682,917 Knuniants et al. — Here the uracil is directly reacted with fluorine in acetic acid in inert gas conditions.

UK British Pat. No. 1,168,391 — This British patent lacks the direct fluorination to form the completed molecule in the last step.

As noted above in British 1,168,391, Ftorafur has been synthesized by a condensation of the bis-trimethylsilyl derivative of 5-fluorouracil and 2-chlorotetrahydrofuran. The present process is an alternate synthetic route to this compound using a direct fluorination of 1-(tetrahydro-2-furanyl)uracil as the terminal reaction. By this route improved yields up to 65% have resulted in a more facile procedure.

PROTOCOL

All melting points (Thomas-Hoover) are uncorrected. Pmr: Varian A-60 spectrometer ($^2H_6$ dimethylsulfoxide as solvent and DSS as internal standard). Uv: Beckman DK-2 spectrophotometer. All glassware used for the reactions and distillations was dried in an oven at 120° for 1 hour or by the passage of a slow stream of dry nitrogen through the assembled apparatus for 1 hour. All concentrations in vacuo were carried out at 40° C.

EXAMPLE I

Preparation of 2-Chlorotetrahydrofuran (II)

Dry methylene chloride (25 ml) and freshly distilled 2,3-dihydrofuran (21.0 g, 0.3 m) were placed in a 100 ml roundbottomed flask fitted with a gas inlet tube and containing a magnetic stirring bar. The solution was cooled (−78° C., dry ice-acetone bath) and stirred while 0.28 m of dry hydrogen chloride gas was introduced (measured with a gas flowmeter using a flowrate of 150 ml/min for 41.7 min). The colorless solution was stored at −20° C. overnight and then the methylene chloride was distilled off at atmospheric pressure. Fractional distillation under vacuum (water aspirator, 25 mm) yielded the product as a water-white liquid, 45%, b.p. 53°–56.5°/25 mm, $N_D^{25°}$ 1.460. The 2-chloroderivative of tetrahydrofuran was somewhat unstable but could be utilized when stored over molecular sieves (Linde, 4A) at −20° C. for 18 hours and gave good yields during condensation with the bis-trimethylsilyl derivative (I) of uracil.

EXAMPLE II

Preparation of 1-(Tetrahydro-2-furanyl)uracil (III)

In an application of a known procedure as in Sniker et al., "Analogs of Pyrimidine Nucleosides," Chem. Heterocycl. Com., (Russia), Eng. Ed., 5, 130 (1969), uracil (5 g, 44.6 mmoles dried in vacuo at 25° C. for 1 hour), hexamethyldisilane (HMDS, 25 ml) and dry ammonium sulfate (20 mg) were heated at 160° C. for 18 hours. Excess HMDS was distilled off in vacuo (25 mm, oilbath 70° C.), 10 ml of dry xylene was added and then removed by distillation in vacuo. The residue (colorless liquid) was dissolved in 150 ml of dry methylene chloride, the solution cooled to −78° C. and then 2-chlorotetrahydrofuran in excess was added. It is noted that the substitution of the particular solvent methylene chloride gave increased and beneficial results as to yield over the references process (45.5% versus 33% yield). The ratio of 2-chlorofuran to uracil to solvent was 1.08 mmoles : 1 mmole : 1 ml. The reaction mixture was tightly stoppered and allowed to stand at ambient temperature for 3.5 hours. Concentration of the solution in vacuo (aspirator and then oil pump) left an oily residue that was triturated with 50 ml of cold (0° C.) ethyl ether-methanol (10:1) resulting in the separation of a white solid.

This solid was recrystallized from a minimum amount of ethyl acetate to give a yield of pure product of about 45.5% (71% based on recovered uracil) of 1-tetrahydro-2-furanyl uracil. This compound had the following characteristics: m.p. 99°–101° C. (ethyl No. acetate); uv and ir spectral data were consistent with the known literature values noted above in this example; NMR δ 11.3 (brs., 1H, NH); δ7.64 (d, 1H, $J_{5,6} = 8$ Hz, $H_6$); δ6.02 (m, 1H, $H_1'$); δ5.64 (d, 1H, $J_{5,6} = 8$ Hz, $H_5$).

EXAMPLE III

Preparation of 1-(Tetrahydro-2-furanyl)-5-fluorouracil (IV)

A 200 ml round-bottomed flask was fitted with a straight vacuum take off adaptor on top of which was placed a Dewar type condenser fitted with a drying tube. A solution of 1-(tetrahydro-2-furanyl)uracil (III, 4.0 g, 22 mmoles) in AR grade methylene chloride (120 ml) was placed in the flask along with a magnetic stirring bar. The system was flushed with nitrogen while the flask was cooled to −78° C. (dry ice-acetone) and then liquid nitrogen was added to the Dewar condenser. Trifluoromethylhypofluorite (726 ml, 24.2 mmoles) was introduced above the surface of the stirred cold solution for 25 min (flowrate ca 30 ml/min.) A white solid separated from solution and after 25 min no uv absorbing material was observed in the 250–340 nm region. The solution was concentrated in vacuo to afford a white solid, and then a cold (−20° C.) solution of concentrated ammonium hydroxide (13 ml) in methanol (130 ml) was added in one portion. Another portion of methanol was added (about 40 ml) followed by ca 4 g of solid carbon dioxide. Concentration in vacuo gave a white solid that was extracted with hot $CHCl_3$ (3 × 50 ml). After filtration, the combined chloroform extracts were concentrated in vacuo to afford the crude product. The crude product was recrystallized from ethanol (12 ml), 2.65 g (60%), m.p. 164°–166° C. A second recrystallization from a minimum amount of ethanol (23 ml) raised the m.p. to 168°–169° C. No depression in m.p. was observed on admixture of this material with an authentic sample prepared by a different route. The ir, uv, and nmr spectral data of this material were also identical to those of an authentic sample: pmr δ 11.17 (brs, 1H, NH); δ 7.81 (d, $J_{F,6}$, 7Hz, 1H, $H_6$) δ 5.89 (m, 1H, $H_1'$).

The embodiments of this invention in which an exclusive property or privilege is claimed are defined as follows:

1. A process for the production of 1-(tetrahydro-2-furanyl)-5-fluorouracil (Ftorafur) (IV) by direct fluorination of 1-tetrahydro-2-furanyl uracil (III) as a terminal reaction which consists of reacting 2-chlorotetrahydrofuran (II) with 2,4-bis-trimethylsilyl uracil (I) in a halogenated hydrocarbon solvent to product (III) and directly fluorinating (III) with an excess of trifluoromethylhypofluorite under cold conditions of about −78° C. and decomposing the trifluoromethylhypofluorite adduct by means of cold methanol-ammonium hydroxide and separating and extracting (IV) by means of a halogenated hydrocarbon solvent.

2. The process according to claim 1, wherein the halogenated hydrocarbon solvent is selected from the group consisting of lower alkylene halides, chloroform, and carbon tetrachloride.

3. The process according to claim 1, wherein the reaction between (I) and (II) is conducted in methylene chloride as a solvent.

4. The process according to claim 1, wherein compound IV is separated and extracted utilizing hot chloroform as a solvent.

* * * * *